United States Patent [19]
Cockburn et al.

[11] Patent Number: 5,728,124
[45] Date of Patent: *Mar. 17, 1998

[54] MEDICAL NEEDLE FOR USE IN ULTRASOUND IMAGING AND METHOD OF ENHANCING THE VISIBLITY OF SUCH A NEEDLE TO ULTRASOUND

[76] Inventors: John Francis Cockburn, 131 Bastings St., Northcote, Victoria 3070, Australia; Donald Cockburn, 35 North Avenue, Mt. Merrion Co., Dublin, Ireland

[*] Notice: The term of this patent shall not extend beyond the expiration date of Pat. No. 5,549,112.

[21] Appl. No.: 706,986

[22] Filed: Aug. 27, 1996

Related U.S. Application Data

[63] Continuation of Ser. No. 401,625, Mar. 9, 1995, Pat. No. 5,549,112.

[51] Int. Cl.$^6$ ............................................. A61M 37/00
[52] U.S. Cl. ................................................... 604/22
[58] Field of Search ...................... 128/662.03, 662.04, 128/662.05, 662.06, 692; 604/22

[56] References Cited

U.S. PATENT DOCUMENTS

| | | |
|---|---|---|
| 3,556,079 | 1/1971 | Omizo . |
| 4,411,657 | 10/1983 | Galindo . |
| 4,413,993 | 11/1983 | Guttman . |
| 4,790,830 | 12/1988 | Hamacher . |
| 4,838,877 | 6/1989 | Massau . |
| 5,046,503 | 9/1991 | Schneiderman ............... 128/662.06 |
| 5,095,910 | 3/1992 | Powers ............................ 128/662.05 |
| 5,131,394 | 7/1992 | Gehlbach ........................ 128/662.05 |
| 5,209,721 | 5/1993 | Wilk ............................... 128/662.05 |

FOREIGN PATENT DOCUMENTS

| | | |
|---|---|---|
| 0083973 | 7/1983 | European Pat. Off. . |
| 0127781 | 5/1984 | European Pat. Off. . |
| 0278186 | 2/1987 | European Pat. Off. . |
| 0397960 | 11/1990 | European Pat. Off. . |
| 0453251 | 10/1991 | European Pat. Off. . |
| 1321205 | 1/1972 | United Kingdom . |
| 2044107 | 2/1980 | United Kingdom . |
| 2157828 | 10/1985 | United Kingdom . |
| 2255282 | 4/1991 | United Kingdom . |
| 2262238 | 12/1992 | United Kingdom . |
| 8203160 | 9/1982 | WIPO . |
| 9205816 | 9/1990 | WIPO . |

OTHER PUBLICATIONS

Ultrasonics, vol. 26, No. 1, Jan. 26, 1988, Guilford, Surrey, Gr. Britain, pp. 27–30.

*Primary Examiner*—George Manuel
*Attorney, Agent, or Firm*—Richard J. Godlewski

[57] ABSTRACT

A needle inserted into body tissue is rendered visible to a Doppler ultrasound imager by generating a longitudinal oscillation of the fluid column in the needle barrel by means of a transducer which is energised by a signal of frequency 100 Hz to 2 kHz, for example. An image of the needle tip is displayed on a screen.

20 Claims, 1 Drawing Sheet

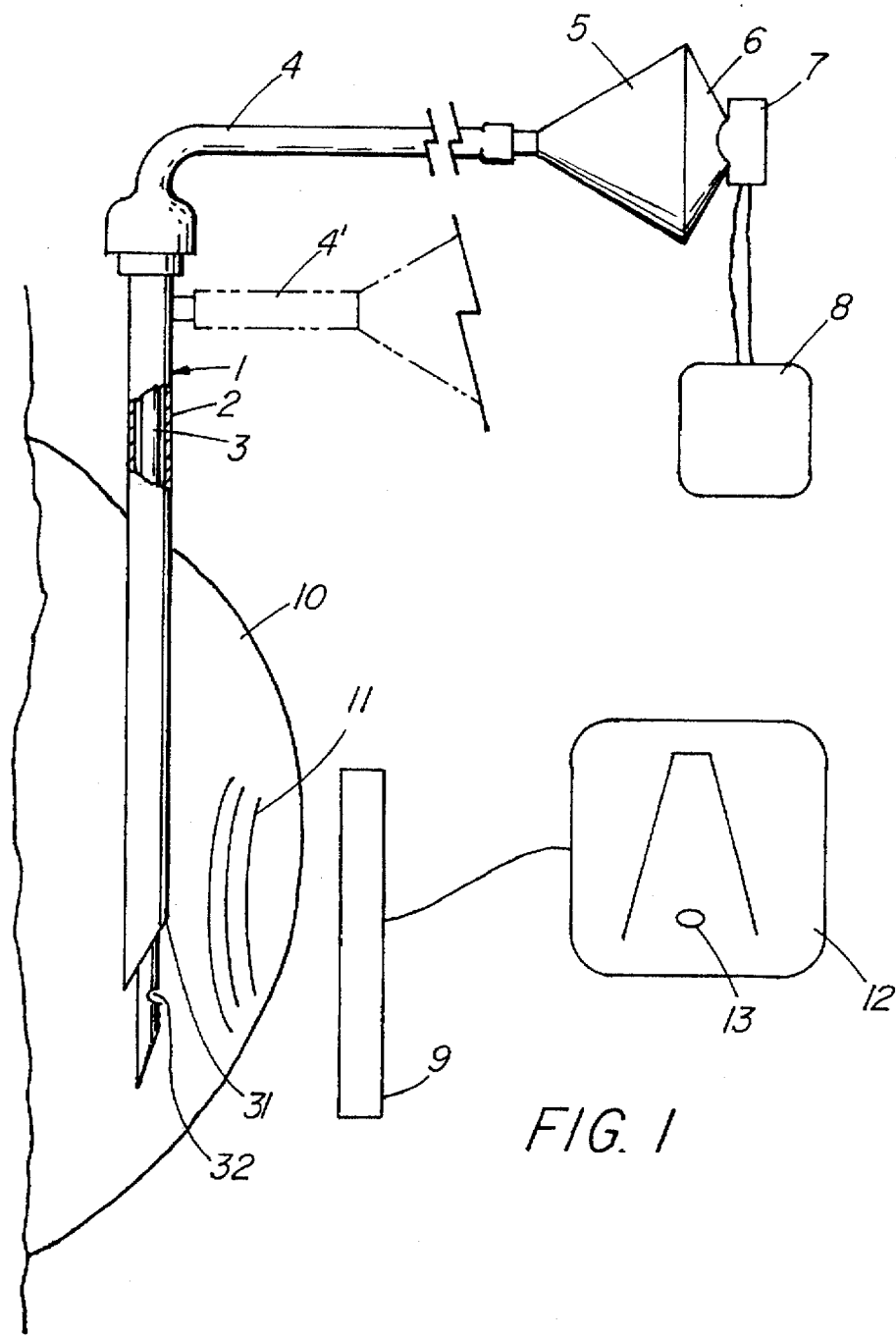
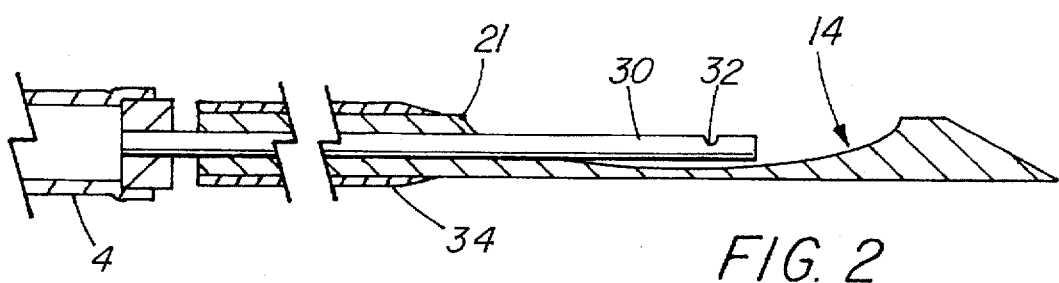

MEDICAL NEEDLE FOR USE IN ULTRASOUND IMAGING AND METHOD OF ENHANCING THE VISIBLITY OF SUCH A NEEDLE TO ULTRASOUND

CROSS-REFERENCE TO RELATED APPLICATION

This is a continuation of patent application Ser. No. 08/401,625 filed Mar. 9, 1995, now U.S. Pat. No. 5,549,112, issued Aug. 27, 1996.

The present invention relates to a hollow medical needle for use in ultrasonic imaging and to a method of enhancing the visibility of such a needle to a Doppler ultrasound imager.

The theory of ultrasonic transmission in biopsy needles is discussed in ULTRASONICS Vol. 26, No. 1, 1988 pp 27 to 30.

U.S. Pat. No. 3,556,079 (Omizo) discloses a medical apparatus comprising a tubular needle within which is mounted an ultrasonic transducer which may be a transmitter, a receiver or a combined transmitter and receiver. This transducer is coupled to saline solution within the needle and transmits and/or detects ultrasound at considerable distances through body tissue at a frequency of e.g. 5 MHz which is subsequently reflected off e.g. flowing blood in a blood vessel and shifted in frequency according to the Doppler equation. If the transducer in the needle is a transmitter only, then an external ultrasound receiver is arranged to detect the reflected Doppler-shifted ultrasound which is demodulated to generate an audio signal whose amplitude is a maximum when the needle is directed at the blood vessel. However the above arrangement merely enables the position of the blood vessel or other target to be detected and does not enable the position of the needle to be detected. It could not, for example, be used to direct a needle towards a portion of diseased static tissue. Furthermore it is not an imaging system.

Ultrasound imaging utilises the principle of sound reflectivity in order to form images of body organs. These images are displayed on the monitor in grey-scale. Some ultrasound machines also incorporate the principle of Doppler frequency shift which allows moving objects eg red blood cells in a blood vessel to be imaged. Such vessels can then be assigned a colour according to the direction of movement within them, and they appear in colour against the grey-scale background of their environs.

It is often desirable to form such an image during treatment with an aspiration or a biopsy needle and it has been found difficult to produce a clearly defined image of the needle by this technique. It has been proposed to apply a transverse vibration to the needle in order to overcome this problem but this does not result in a clear image of the needle tip.

GB-A-2,157,828 discloses an ultrasonic imaging apparatus comprising an inner needle having a miniature ultrasonic transducer mounted at its tip and an outer tubular puncture needle surrounding and supporting the inner needle. An ultrasonic imager generates an ultrasonic beam which impinges on the miniature transducer and the resulting electric output signal is either used to trigger a transponder which causes the transducer to emit a predetermined ultrasonic signal which is detectable and locatable by the imager or to enable circuitry in the imager to detect the position of the needle from the time interval between emission and detection of the ultrasonic beam. From this information the position of the needle can be superimposed on the image.

However the above arrangement is complex and expensive and in general the needle can be used only with one design of imager.

Further background information is provided in U.S. Pat. No. 5,131,394, EP-A-397,960, EP-A-83,973 (which teaches at p. 7 para 1 the desirability of contact between the stylet and the needle) and WO-A-82/03160, which however lies outside the technical field of the present invention.

EP-A-453,251 discloses a biopsy needle having a solenoid coil coupled to a core which is mounted directly on the proximal end of the stylet and arranged to reciprocate the stylet longitudinally at a frequency of e.g. up to 100 Hz in order to render the needle tip visible to Doppler ultrasound. The amplitude of vibration is such that the tip of the stylet oscillates between a position in which it is flush with the opening of the cannula and a position in which it is retracted about 1 mm into the cannula.

However the above arrangement in which the vibratory transducer is directly coupled to the stylet has the disadvantage that movement of the stylet inevitably causes motion of similar amplitude and frequency in the cannula, with the result that the motion is not confined to the needle tip and the Colour Doppler imager assigns a flare of colour to the entire needle. Furthermore the weight of the solenoid makes the needle harder to manipulate, an important point when one considers the degree of accuracy needed to perform certain biopsies.

Accordingly the present invention provides a medical apparatus comprising:

a) a tubular needle for insertion into body tissue, said needle having a bore in communication with said body tissue at a tip region thereof, and b) a sub-ultrasonic transducer for generating a longitudinal oscillation of a fluid column within said bore at a sub-ultrasonic frequency, said transducer being substantially mechanically isolated from said needle. The oscillation generated by the transducer (preferably at an audio frequency) enhances the visibility of the region of the needle tip to Doppler ultrasound imaging.

Preferably the transducer is remote from the needle and is coupled to the needle by a flexible tube which contains a further fluid column (preferably an air column) coupled to the transducer. Such an elastic coupling enables the tissue to be characterised by its Doppler image, as described below in detail.

In another aspect the invention provides a kit of parts for the above apparatus.

In another aspect the invention provides a method of enhancing the visibility to Doppler ultrasound imaging of the tip and/or adjacent tissue of a tubular needle inserted into a human or animal body comprising generating a longitudinal oscillation of a fluid column within said needle at a frequency which is lower than the frequency of the ultrasound emitted by the Doppler ultrasonic imager by means of a transducer which is substantially mechanically isolated from the needle.

Since the colour of a region of a Doppler ultrasound image is dependent on the velocity of the corresponding region of tissue and this velocity will vary with the amplitude of the oscillation of the end of the fluid column at the needle tip (assuming that the period of the oscillation is fixed) and this amplitude in turn is dependent on the mechanical properties of the tissue being vibrated by the fluid column, the apparatus of the present invention should enable the tissue at the needle tip to be characterised. For example, fatty tumours will vibrate differently from solid lesions and would be expected to generate a different colour response in the Doppler image of the needle tip.

Accordingly, in another aspect the invention provides a method of enhancing the visibility to Doppler ultrasound imaging of the tip and/or adjacent tissue of a tubular needle inserted into a human or animal body, comprising generating a longitudinal oscillation of a fluid column within said needle at a frequency which is lower than the frequency of the ultrasound emitted by the Doppler ultrasonic imager by means of a transducer which is arranged to vary the amplitude of said oscillation in dependence upon the mechanical properties of the tissue. This is most easily achieved by coupling the transducer to a column of air or other gas in a tube which communicates with the bore of the needle.

The transducer may for example comprise a moving coil loudspeaker coupled to the fluid column in the needle bore by a connecting tube whose cross section decreases towards the needle and thereby amplifies the motion of the loudspeaker diaphragm. Alternatively a thermal transducer such as a spark-gap chamber or a piezoelectric transducer may be used.

The optimum frequency of the longitudinal oscillation generated by the transducer of the needle arrangement will depend on the Colour Doppler ultrasonic imager with which it is being used, in particular on the velocity range detectable by the imager. In a typical Colour Doppler ultrasonic imager the minimum detectable velocity will be of the order of +/−0.001 m/s and a maximum velocity of about +/−3.8 m/s, with a more usual range being from +/−0.02 m/s to +/−0.6 m/s. Accordingly it is believed that the frequency and amplitude of oscillation should be such that the maximum velocity is within ve ranges. With conveniently achievable amplitudes of oscillation, it is believed that the most useful frequencies will be in the audio range i.e. 20 Hz to 20 kHz but the invention is by no means limited to the above ranges.

Preferred embodiments of the invention are described below by way of example only with reference to the accompanying drawing, wherein:

FIG. 1 is a diagrammatic representation of a medical apparatus in accordance with the invention, and FIG. 2 is a longitudinal cross-section of another needle arrangement for use in the arrangement of FIG. 1.

Referring to FIG. 1, which is a purely diagrammatic representation, a hollow needle 1 is shown inserted into body tissue 10. The needle comprises a 22 gauge tubular cannula 2 having an outside diameter of 0.711 mm (0.028") and housing a stylet 3 of 0.457 mm (0.018") diameter within the cannula. The tip of the stylet projects about 2 mm beyond the tip 31 of the cannula. The stylet is hollow and has an eccentric opening 32 immediately adjacent to its closed bevelled tip. The eccentric opening, which protrudes beyond the end of the 22 gauge housing cannula, allows the oscillating air column to deliver movement to adjacent tissue while minimising the possibility of body tissue entering the stylet and occluding it. This arrangement allows the tip of the stylet to be rendered visible to Doppler ultrasound during the insertion of the needle through tissue. 8 mm flexible pressure tubing 4 connects the hollow stylet with the neck of a funnel member 5 as shown. Alternatively the stylet 3 may optionally be solid and after passage of the needle through tissue, the solid stylet may be removed and the bore of the cannula 2 may be connected directly to the pressure tubing (4') and funnel member as shown in phantom. The mouth of funnel member 5 is coupled in an airtight manner to a moving coil loudspeaker 7 whose diaphragm 6 is driven by a signal from a signal generator 8.

Preferably the signal, which may be a pulsed or an oscillating signal, has a period of 0.03 s to 0.001 s. More preferably the signal has a sine, square or triangular waveform of frequency 333 Hz to 1 kHz (ideally 400 to 800 Hz e.g. 600 Hz) and a power of a few (e.g. 100) mW.

The body tissue is insonated with an ultrasonic beam 11 by a Doppler ultrasound imager 9, which may for example be an Acuson 128XP10 imager. An image 13 of the needle tip 31 is formed on a screen 12 of the imager.

EXAMPLE

A working model utilising a jelly phantom in place of the body tissue 10 was constructed generally as shown in FIG. 1. The components of the working model were as follows: hollow needles, a hollow stylet, a loudspeaker, signal generator and 50 cm of 'pressure' tubing. The needles were standard 15 cm Chiba needles (Cook Inc., Bloomington Ind.) in 18, 20, and 22G sizes and the 15 cm hollow stylet was made of superelastic nickel titanium alloy with an inner diameter of 0.406 mm (0.016") (Raychem Corp., Menlo Pk. Calif.). The speaker coil was modified from a 127 mm (5 inch) diameter plastic-coned loudspeaker (Tannoy Ltd., Strathclyde, Scotland) and was connected in an airtight arrangement via a funnel to the hollow stylet. The signal generator used was a Korg 770 synthesiser (Keio Electronic Laboratory Corporation, Tokyo, Japan). This instrument generates square, triangular and rectangular waveforms at a wide range of audio frequencies. The signal was amplified through a Realistic SA 1500 audio amplifier (Tandy Corporation, Fort Worth, Tx.).

Colour Doppler ultrasound machines used to evaluate the device were an Acuson XP10 (Acuson Ltd.),and a Diasonics Spectra VST (Diasonics Ltd. Milipitas Calif. USA). Testing was done by applying a 3.5 MHz probe to a jelly phantom and immobilising it in position. The pressure tubing was then connected directly to the needle barrel (minus its matching solid stylet). The needle was then inserted into the phantom as far as possible. 5 MHz and 7.5 MHz probes were also used with the needle with similar results. Signal was applied to the needle starting at 1Hz and gradually increasing in frequency until colour signal was registered by the ultrasound machine at a selected pulse repetition frequency and gain setting.

Results

The needle tip was displayed as a beacon of colour regardless of the angle of incidence of the Doppler beam. Transverse, longitudinal and oblique projections displayed the beacon equally. The colour signal was not constant but was found to change hue and to flicker at varying rates depending on the frequency of the sound wave applied to the needle. This is believed to be caused by an interference pattern at the needle tip between the frequency of motion and the pulse repetition frequency of the incoming Doppler wave. The needle tip was readily detectable when inserted fully into the phantom. This corresponded to a depth of 15 cm. No signal other than that at the tip of the needle was registered when the needle was stationary.

It was found that a frequency of 600 Hz yielded a beacon of signal which was readily detectable at pulse repetition frequencies ranging from 800 to 2250 kHz using the Diasonics machine. Within this range, colour gain values of between 68 and 80 dB were required to demonstrate a visible beacon unaccompanied by colour noise on the screen. There was no visible difference between sine, square, triangular or rectangular waveforms. Many other frequencies were found to generate detectable signal at various pulse repetition frequencies and colour gain settings but 600 Hz was the single frequency most likely to be detectable in the range of pulse repetition frequencies described.

Increasing gain values above 80 dB led to colour noise which could be mistaken for the needle tip. Below a pulse repetition frequency of 800 kHz useful signal at the tip uncorrupted by colour noise was demonstrated only at 400 Hz with this particular apparatus. Above 2,250 Hz a similar problem occurred with this particular apparatus. Because pulse repetition frequencies are not given a numerical value on the Acuson XP10 display it was not possible to directly correlate the findings between it and the Diasonics Spectra VST. It was found that the Acuson machine was capable of displaying the colour beacon at the tip of the needle as well as the Diasonics although differences in frequency response between these two machines could not be ruled out because the frequency of pulse repetition is not displayed on the Acuson machine.

At higher pulse repetition frequencies (greater than 1000 Hz) tissue motion 'flash' was not prominent and did not obscure the signal at the needle tip when Doppler interrogation was performed during the process of needle insertion. At pulse repetition frequencies lower than 1000 Hz, an increasing amount of tissue flash was seen with needle movement which at the lowest settings e.g. 100 Hz was very prominent.

It was found that when a tissue or agar phantom was used, the needle accumulated material within it and became blocked during insertion. When this occurred, no colour signal was visible at the tip. Blockage was prevented by using a phantom made of ultrasound coupling jelly.

The 0.406 mm (0.016") internal diameter hollow stylet was connected to the pressure tubing and inserted into the 20G Chiba needle so that it protruded just beyond its tip to see if it was possible to conduct signal down a lumen of this diameter. Satisfactory colour signal was easily visible at the tip of this hollow stylet, although the size of the beacon was smaller than when the 20G needle barrel was connected directly to the pressure tubing.

The volume control of both amplifier and signal generator needed to be at maximum in order for good quality signal to be registered. Accordingly the speaker was housed in a cabinet to minimise unwanted sound output. Reducing the volume caused a corresponding reduction in colour signal on the monitor. Of interest is the observation that slight movement of the transducer off the needle tip resulted in failure to detect any signal. This sensitivity allowed detection of the exact location of the tip of the needle in both colour Doppler and spectral modes. Furthermore the needle tip could be easily found when the probe was displaced far away from the insertion site and aligned randomly with respect to the needle shaft.

Referring now to FIG. 2, the needle arrangement shown is designed to prevent occlusion of the oscillating fluid column during insertion into the body tissue and comprises a tubular outer cutting sheath 34 housing a trocar 21. Trocar 21 has a recess 14 at its distal end which exposes a retractable tubular stylet 30 which has a radially directed aperture 32 adjacent its forward (distal) tip. The bore of stylet 30 communicates with the funnel arrangement shown in FIG. 1 via flexible tubing 4 and consequently the Doppler signal is emitted at aperture 32 throughout the insertion and enables the precise position of the tip portion of the needle arrangement to be detected continuously.

In use, first the trocar 21 is advanced together with the stylet 30, the latter having its aperture 32 located in the recess 14 as shown and the outer cutting sheath being retracted as shown. When the recess 14 has been advanced to the required position, as determined with the aid of the Doppler ultrasound image of the stylet tip region, the stylet 30 is withdrawn from the trocar 21 to allow tissue to fill the recess 14 and outer cutting sheath 34 is advanced (from left to right relative to FIG. 2) over the trocar to cut off the tissue lying in recess 14. The resulting tissue sample can then be extracted. In this manner a tissue sample (e.g. of a liver lesion) can be taken from an accurately known region of the tissue.

In all the arrangements illustrated in the drawings, the stylet, cannula and trocar (if used) as well as the flexible tubing are sterilised and may be disposable.

The invention also provides a medical apparatus comprising a tubular needle which is adapted for insertion into body tissue, the needle being provided with a transducer which is substantially mechanically isolated from the needle and coupled to a fluid column within the needle, the transducer being arranged to generate a longitudinal oscillation of said fluid column at a non-ultrasonic frequency which enhances the visibility of the needle tip to Doppler ultrasound imaging.

We claim:

1. A medical needle arrangement for insertion into body tissue, comprising:

a hollow stylet having a bore therein, a distal ends and an exposed aperture positioned about said distal end and communicating with said bore, said aperture being located and dimensioned to substantially prevent occlusion of said aperture by body tissue, said bore and said aperture being configured for emitting a sub-ultrasonic longitudinal oscillation therefrom; and a cannula, said stylet being housed within and slidable relative to said cannula.

2. The medical needle arrangement of claim 1 wherein said exposed aperture of said hollow stylet protrudes beyond a distal end of said cannula.

3. The medical needle arrangement of claim 1 wherein said distal end of said hollow stylet includes a closed beveled tip.

4. The medical needle arrangement of claim 1 wherein said cannula includes a beveled distal end.

5. The medical needle arrangement of claim 1 wherein said aperture is a radial aperture formed in a wall of said hollow stylet.

6. The medical needle arrangement of claim 1 wherein said hollow stylet comprises a tubular stylet.

7. The medical needle arrangement of claim 1 wherein said cannula comprises a trocar having a recess about a distal end thereof and wherein said exposed aperture of said hollow stylet is positioned in said recess of said trocar for emitting a sub-ultrasonic longitudinal oscillation therefrom.

8. The medical needle arrangement of claim 7 wherein said exposed aperture comprises a radially directed aperture.

9. The medical needle arrangement of claim 7 further comprising an outer cutting sheath being slidable over said recess of said trocar.

10. The medical needle arrangement of claim 1 further comprising means for applying a sub-ultrasonic longitudinal oscillation to said bore of said hollow stylet.

11. The medical needle arrangement of claim 1 wherein said cannula includes a bore and wherein said arrangement further comprises means for applying a sub-ultrasonic longitudinal oscillation to said bore of said cannula.

12. The medical needle arrangement of claim 1 further comprising means for substantially mechanically isolating said hollow stylet and said cannula from a sub-ultrasonic transducer.

13. A medical needle arrangement for insertion into body tissue, comprising:

- a hollow stylet having a bore therein, a distal end, and an exposed aperture positioned about said distal end and communicating with said bore; and
- a trocar having a recess about a distal end thereof, said stylet being housed within and slidable relative to said trocar, wherein said exposed aperture of said hollow stylet is positioned in said recess of said trocar for emitting a sub-ultrasonic longitudinal oscillation therefrom.

14. The medical needle arrangement of claim 13 wherein said exposed aperture comprises a radially directed aperture.

15. The medical needle arrangement of claim 13 further comprising an outer cutting sheath being slidable over said recess of said trocar.

16. The medical needle arrangement of claim 13 further comprising means for applying a sub-ultrasonic longitudinal oscillation to said bore of said hollow stylet.

17. The medical needle arrangement of claim 13 wherein said distal end of said trocar includes a closed beveled tip.

18. The medical needle arrangement of claim 13 wherein said aperture is a radial aperture formed in a wall of said hollow stylet.

19. The medical needle arrangement of claim 13 wherein hollow stylet comprises a tubular stylet.

20. A medical needle arrangement for insertion into body tissue, comprising:

- a tubular stylet having a bore therein, a distal end, and an exposed aperture positioned about said distal end and communicating with said bore;
- a trocar having a recess about a closed, distal end thereof, said tubular stylet being housed within and slidable relative to said trocar, wherein said exposed aperture of said tubular stylet is positioned in said recess of said trocar for emitting a sub-ultrasonic longitudinal oscillation therefrom; and
- an outer cutting sheath being slidable over said recess of said trocar.

* * * * *